US00PP17164P2

(12) United States Plant Patent
Meyer

(10) Patent No.: US PP17,164 P2
(45) Date of Patent: Oct. 24, 2006

(54) ***HEMEROCALLIS* PLANT NAMED 'GOING BANANAS'**

(50) Latin Name: *Hemerocallis (Kaempfer) hybrida*
Varietal Denomination: Going Bananas

(75) Inventor: Chris Meyer, Zeeland, MI (US)

(73) Assignee: Walters Gardens, Inc., Zeeland, MI (US)

( * ) Notice: Subject to any disclaimer, the term of this patent is extended or adjusted under 35 U.S.C. 154(b) by 58 days.

(21) Appl. No.: 11/236,073

(22) Filed: Sep. 27, 2005

(51) Int. Cl.
*A01H 5/00* (2006.01)

(52) U.S. Cl. ..... Plt./312
(58) Field of Classification Search ..... Plt./312
See application file for complete search history.

*Primary Examiner*—Kent Bell
*Assistant Examiner*—Annette H Para

(57) ABSTRACT

A new and distinct Daylily plant named 'Going Bananas' characterized by full, light-yellow, fragrant flowers, on compact plants that bloom for at least 16 weeks during the growing season and are suitable for landscape or potted culture use.

2 Drawing Sheets

Botanical classification: *Hemerocallis* (Kaempfer) *hybrida.*
Variety denomination: 'Going Bananas'.

SUMMARY, BACKGROUND AND ORIGIN OF THE PLANT

The new and distinct *Hemerocallis* cultivar 'Going Bananas', hereinafter also referred to as 'Going Bananas' and "the plant" is a new and distinct plant. It was hybridized by Chris Meyer in the summer of 1992, and discovered as first flowered in 1994 as part of an on-going hybridizing program to develop new and improved cultivars. The plant was found growing in trial fields of a nursery in Zeeland, Mich., USA. The plant has been successfully propagated by division methods at the same nursery to produce identical plants that maintain the unique characteristics of the original plant.

BRIEF DESCRIPTION OF THE DRAWINGS

The photographs of the new invention demonstrate the overall appearance of the plant, including the unique traits. The colors are as accurate as reasonably possible with color reproductions. Ambient light spectrum, source and direction may cause the appearance of minor variation in color.

GENERAL DESCRIPTION OF THE PLANT

Figure 1:
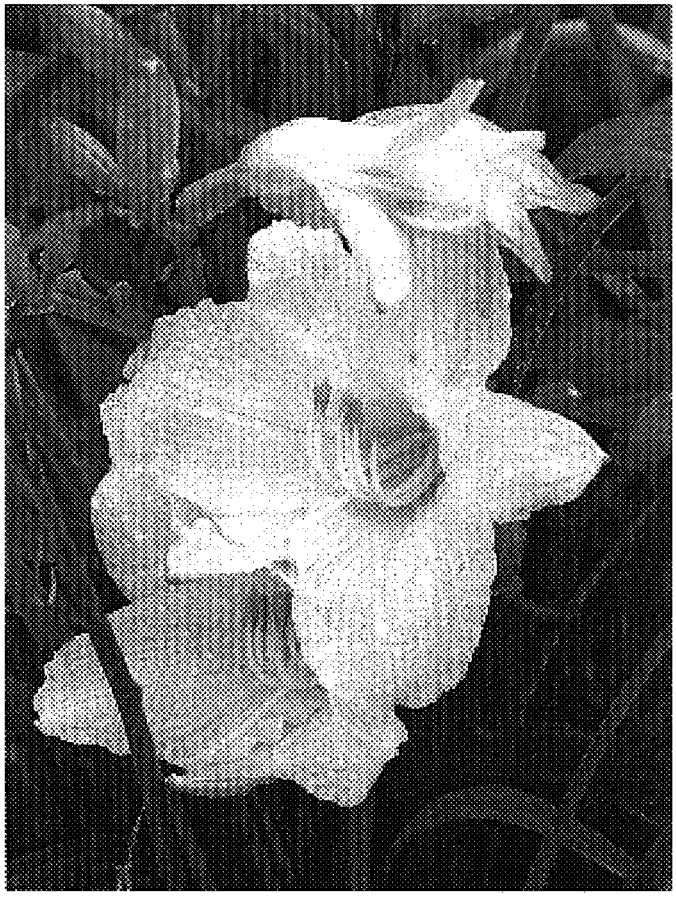
FIG. 1 shows a close-up of the flowers of the plant.
Figure 2:
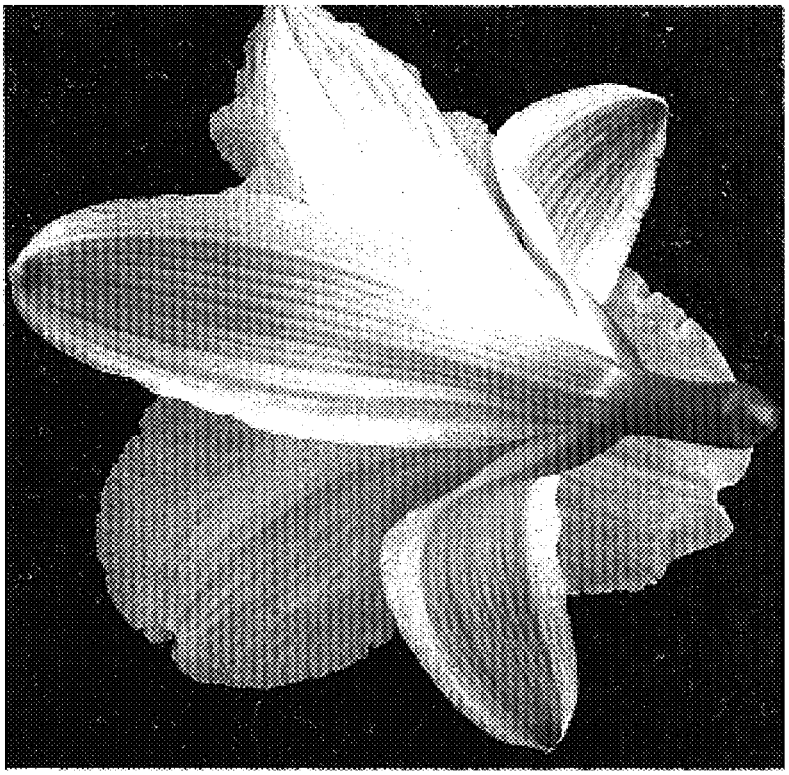
FIG. 2 shows the reverse side of the flower.
Figure 3:
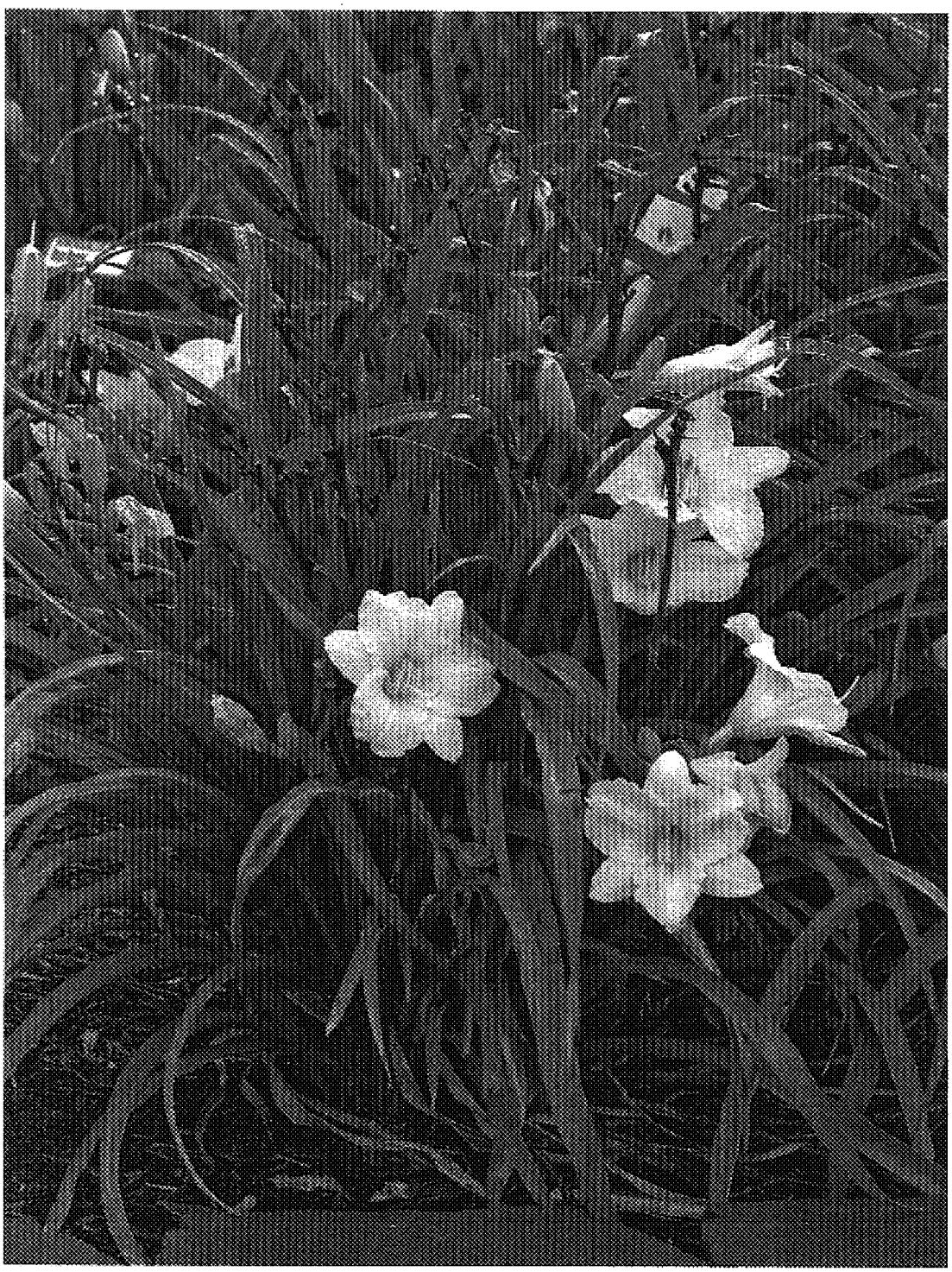
FIG. 3 shows the overall plant.

The genus *Hemerocallis* is mainly native to central Europe, China and Japan with approximately 15 species. It is now highly hybridized with over 60,000 registered named cultivars. *Hemerocallis* 'Going Bananas' is unique from all forms known to the applicant in the following characteristics:

1. Light yellow flowers up to 9 mm across
2. Fully over-lapping tepals
3. Extremely long bloom season
4. Lightly creped petals 5. Short habit with flowers just above foliage
6. Light sweetly fragrant flowers
7. Freely opening flowers

COMPARISON TO NEAREST CULTIVARS

The nearest comparison cultivar known to the hybridizer is *Hemerocallis* 'Happy Returns' (not patented). In comparison, 'Going Bananas' is a slightly larger plant overall, has larger flowers and tepals with lighter yellow coloring to the front, more green on the back and more creping on the inner tepals, and it does not stop flowering in August as 'Happy Returns' frequently does.

DETAILED BOTANICAL DESCRIPTION

The following descriptions and color references are based on the 2001 edition of The Royal Horticultural Society Colour Chart except where common dictionary terms are used. The new plant, *Hemerocallis* 'Going Bananas', has not been observed under all possible environmental conditions. The phenotype may vary slightly with different environmental conditions, such as temperature, light, fertility, moisture and maturity levels, but without any change in the genotype. The following observations and size descriptions are of three-year old plants, field grown plant in sandy loam soil with supplemental irrigation and fertilizer in a test garden in Zeeland, Mich., USA. Normal summer daytime high temperatures ranging between 24 to 34 degrees C., and nighttime low temperatures of 9 to 20 degrees C.

Botanical classification: *Hemerocallis*×hybrid cultivar 'Going Bananas'.

Parentage: 'Happy Returns' (not patented) (female)× 'Brocaded Gown' (not patented) (male).

Propagation: Asexual division of the rhizome in mid summer.

*Time to initiate roots from division.*—Two to three weeks.

*Crop time.*—Under normal growing conditions about 2 years to produce 8 to 10 divisions; Plant vigor is very good to high.

*Rooting habit*.—Normal, fleshy up to 5 mm thick with thick storage portions 4.5 to 6 cm long and 1.0 to 1.2 cm in diameter, lightly branching with thin rootlets of 1 to 2 mm in diameter.

Plant description:

*Plant shape and habit*.—Hardy, deciduous, winter dormant, herbaceous rhizomatous perennial with basal linear leaves arching in upper ⅔'s. Natural foliage spread is 55 to 70 cm in diameter and 50 to 55 cm tall with an occasional leaf up to 58 cm tall, symmetrical. Each flower is well separated on the scape from the next flower to assure complete opening.

Foliage description:

*Shape and size*.—Linear, narrowly acute apex, entire, glabrous, without petiole; 1 to 4 cm wide in center, up to 84 cm long tapering to point; 8 to 10 per division.

*Color*.—Young leaves top and bottom surfaces about RHS 137 B with a slight glaucous surface; older leaves top and bottom RHS 137 A, without glaucous surface.

*Venation*.—Parallel; same color as surrounding leaf surface. Flower description: epigynous, flared funnelform up to 9 cm diameter; opening in evening with tepal in the six o'clock position more protruded from flower face than other tepals; flowering in Michigan begins mid June and continuing through mid October or hard freeze.

*Buds*.—Long ovoid, with a constricted portion toward the base that is 1.5 cm long and 7 mm in diameter; main bud is up to 16.5 cm long and 1.5 cm at the widest portion 2 days before opening; RHS 144 C in the center, RHS 141 A at the apex, RHS N144 C before the constricted portion, and longitudinal edges of joined tepals are RHS 3 C.

*Flower duration*.—Opening in the evening and lasting for more than 24 hours on plant or as cut flower.

*Peduncle*.—Erect to 65 cm tall, nearly round in cross section and up to 1 cm in diameter, green color RHS 144 A with 10 to 15 flowers spaced with up to triple branching; 10 to 14 peduncles per two-year old plant and up to 22 on a three-year old plant per season.

*Pedicel*.—Approximately 5 mm long, 4 mm wide, RHS 143 A.

*Tepals*.—Six, in two sets of three; Outside set of three — entire, smooth surface, narrowly oblong with acute apex, fused in last 2 cm toward base, 6.0 to 6.5 cm long and 3 cm wide, front color is uniform RHS 6 C; back RHS 6 C to RHS 6 D on the perimeter 5 mm, with apical 3 mm of tip RHS 141 B, the central middle portion closest to RHS 151 C, and the basal center portion RHS 151 A.

*Inside set of three*.—Entire, oblong with rounded apex, creped texture in perimeter 1 cm; 5 cm wide and 6.5 cm long; front, RHS 5 B becoming lighter within 3 mm of base to RHS 1 B and having a lighter colored 2 mm wide midrib of RHS 4 C; back RHS 2 C blending to RHS 6 D starting within 5 mm of the base.

*Gynoecium*.—Single.

*Style*.—9 to 10 cm long; 2 mm diameter tapered toward apex; slightly curved upward at distal end; RHS 4 B with some light green undertone.

*Stigma*.—1 to 2 mm diameter, RHS 4D.

*Androecium*.—Six.

*Filaments*.—Six; fused at base with petals; slightly curved upward at distal end; 4.5 cm to 5.0 cm long; round at apex to 1 mm in diameter; flatted at base to 4 mm wide; RHS 9 C.

*Anthers*.—6 to 7 mm long; 1.5 mm wide; about RHS N77 A at the dehiscing fissure and lighter than RHS 84 C at the point of attachment to the filament.

*Pollen*.—Yellow-orange RHS 17 B.

*Fragrance*.—Lightly sweet, similar to *Hemerocallis* 'Hyperion' (non-patented).

*Seeds*.—Near black, ovoid to about 5 mm long; typically 12 to 18 per pod; in ovoid to slightly globose pods between RHS 165 A and RHS 165 B, up to 3.5 cm long.

Disease resistance: The plant grows best with plenty of moisture and adequate drainage, but is able to tolerate drought and moderately wet soil. Winter hardy to at least USDA zone 3 through 9. Flowers resistant to water spots. Other disease resistance is typical of other daylilies.

I claim:

1. A new and distinct cultivar of ornamental Daylily plant named 'Going Bananas' as herein described and illustrated, with fragrant light yellow flowers on compact plants for an extended period, suitable as a potted plant or garden landscaping.

* * * * *